(12) United States Patent
Warner

(10) Patent No.: US 12,704,490 B2
(45) Date of Patent: Aug. 11, 2026

(54) GAS DETECTOR WITH REMOVABLE SENSOR ASSEMBLY

(71) Applicant: Carrier Corporation, Palm Beach Gardens, FL (US)

(72) Inventor: Tanner Warner, Chanhassen, MN (US)

(73) Assignee: DETECTOR ELECTRONICS BUYER US, LLC, Stamford, CT (US)

( * ) Notice: Subject to any disclaimer, the term of this patent is extended or adjusted under 35 U.S.C. 154(b) by 440 days.

(21) Appl. No.: 18/365,161

(22) Filed: Aug. 3, 2023

(65) Prior Publication Data

US 2024/0044855 A1 Feb. 8, 2024

Related U.S. Application Data

(60) Provisional application No. 63/370,434, filed on Aug. 4, 2022.

(51) Int. Cl.
*G01N 33/00* (2006.01)
*G01D 11/24* (2006.01)

(52) U.S. Cl.
CPC ....... *G01N 33/0009* (2013.01); *G01D 11/245* (2013.01)

(58) Field of Classification Search
CPC ............. G01D 11/245; G01N 33/0009; G01N 33/0027
USPC ........................................................ 73/431
See application file for complete search history.

(56) References Cited

U.S. PATENT DOCUMENTS 11,686,674 B2 * 6/2023 Bryzgalov ......... G01N 33/0027 250/352
2003/0224643 A1 12/2003 Starta et al.
2009/0211357 A1 8/2009 Pinto et al.
2012/0192623 A1 * 8/2012 Adami ................ G01N 33/007 73/31.05
2015/0143901 A1 5/2015 Matsui et al.
2015/0377658 A1 12/2015 Landis
2017/0299545 A1 * 10/2017 Mostoller .......... H01R 12/7076

FOREIGN PATENT DOCUMENTS

EP 4170343 A1 4/2023
KR 20110009120 A * 1/2011 ......... G01L 19/0038
WO WO-2009121426 A2 * 10/2009 ......... G01L 19/0084

OTHER PUBLICATIONS

Machine translation of WO 2009121426 (Year: 2009).*
Machine translation of KR 20110009120 (Year: 2011).*
Partial European Search Report for Application No. 23189333.0, Issued Dec. 5, 2023, 8 Pages.
European Search Report for Application No. 23189333.0, Issued Mar. 5, 2024, 10 Pages.

* cited by examiner

*Primary Examiner* — Nathaniel J Kolb
(74) *Attorney, Agent, or Firm* — CANTOR COLBURN LLP

(57) ABSTRACT

A gas sensor assembly is disclosed. In some embodiments, the gas sensor assembly comprises a sensor housing, the sensor housing configured to house a gas sensor and a sensor circuit, wherein the gas sensor and the sensor circuit are configured to be detachably connected. The gas sensor assembly further comprises a cover, the cover configured to be detachably connected to the sensor housing, wherein the cover is configured to hold the gas sensor in place within the sensor housing.

18 Claims, 2 Drawing Sheets

100
120
122
122
124
127
130
131
132
134
135
137
138
138
150
160
165

GAS DETECTOR WITH REMOVABLE SENSOR ASSEMBLY

CROSS REFERENCE TO A RELATED APPLICATION

The application claims the benefit of U.S. Provisional Application No. 63/370,434 filed Aug. 4, 2022, the contents of which are hereby incorporated in their entirety.

BACKGROUND

The invention relates generally to gas detectors and, more specifically, to gas detectors with a removable sensor assembly.

Gas detectors generally include a gas sensor assembly having a gas sensor and a sensor circuit. To change the gas sensor (e.g., because of malfunction, because of a sensor's limited lifespan, or if the gas detector is used to detect a different gas), the gas sensor assembly is generally removed from the gas detector and replaced with a different gas sensor assembly.

BRIEF DESCRIPTION

Aspects of the disclosure relate to methods, apparatuses, and/or systems for a gas sensor assembly in gas detectors.

In some embodiments, a gas sensor assembly comprises a sensor housing, the sensor housing configured to house a gas sensor and a sensor circuit, wherein the gas sensor and the sensor circuit are configured to be detachably connected. The gas sensor assembly further comprises a cover, the cover configured to be detachably connected to the sensor housing, wherein the cover is configured to hold the gas sensor in place within the sensor housing.

In some embodiments, the gas sensor is configured to be removed from the gas sensor assembly when the cover is disconnected from the sensor housing.

In some embodiments, the cover is configured to maintain a connection between the sensing interface and the sensor circuit, such that responsive to the cover being at least partially disconnected from the sensor housing, the sensing interface is at least partially disconnected from the sensor circuit.

In some embodiments, the cover is configured to apply a pressure against the sensing interface to maintain the connection between the sensing interface and the sensor circuit.

In some embodiments, the cover comprises a base element, the base element configured to interface with a bottom end of the sensor housing, such that the base element extends inward to support a portion of the gas sensor.

In some embodiments, the sensor housing comprises a side wall; the cover comprises a projecting element; and the cover is configured to be detachably connected to the sensor housing such that the projecting element interfaces with a portion of the side wall.

In some embodiments, the base element is configured to cover the bottom end of the sensor housing and extend inward beyond the bottom end to form a partial shelf to support the sensing interface.

In some embodiments, a gas detector comprises a gas sensor assembly as described herein.

In some embodiments, a method for manufacturing a gas sensor assembly comprises providing a sensor housing, the sensor housing configured to house a gas sensor and a sensor circuit, wherein the gas sensor and the sensor circuit are configured to be detachably connected; and providing a cover, the cover configured to be detachably connected to the sensor housing, wherein the cover is configured to hold the gas sensor in place within the sensor housing.

Various other aspects, features, and advantages of the invention will be apparent through the detailed description of the invention and the drawings attached hereto. It is also to be understood that both the foregoing general description and the following detailed description are examples and not restrictive of the scope of the invention.

DETAILED DESCRIPTION

In the following description, for the purposes of explanation, numerous specific details are set forth in order to provide a thorough understanding of the embodiments of the invention. It will be appreciated, however, by those having skill in the art that the embodiments of the invention may be practiced without these specific details or with an equivalent arrangement. In other cases, well-known structures and devices are shown in block diagram form in order to avoid unnecessarily obscuring the embodiments of the invention.

The disclosure, in accordance with some embodiments, describes a gas sensor assembly. Existing gas detectors, generally include removable gas assemblies that are replaced if one component of the assembly needs replacing. For example, in the event of a failure of the gas sensor, the entire gas sensor assembly is replaced regardless of whether the other components need replacing or not. This may not be effective because it requires more components than needed (e.g., only the sensor itself needs replacing).

As will be described herein, in some embodiments, the gas sensor assembly of the disclosure may allow for access to the gas sensor (e.g., for removal and/or replacement) by removing a single part and without disturbing the other components of the sensor assembly. The gas sensor assembly of the disclosure may help in reducing the number and cost of components to be replaced. In some embodiments, the gas sensor assembly may include a gas sensor, a gas circuit board, a sensor housing, and a housing cover. The cover may be configured to detachably connect to the housing, thereby allowing access to the gas sensor for removal and/or replacement. The cover may be configured to support and/or keep the gas sensor in place inside the sensor housing. This may allow for easy removal and/or replacement without requiring tools.

Figure 1:
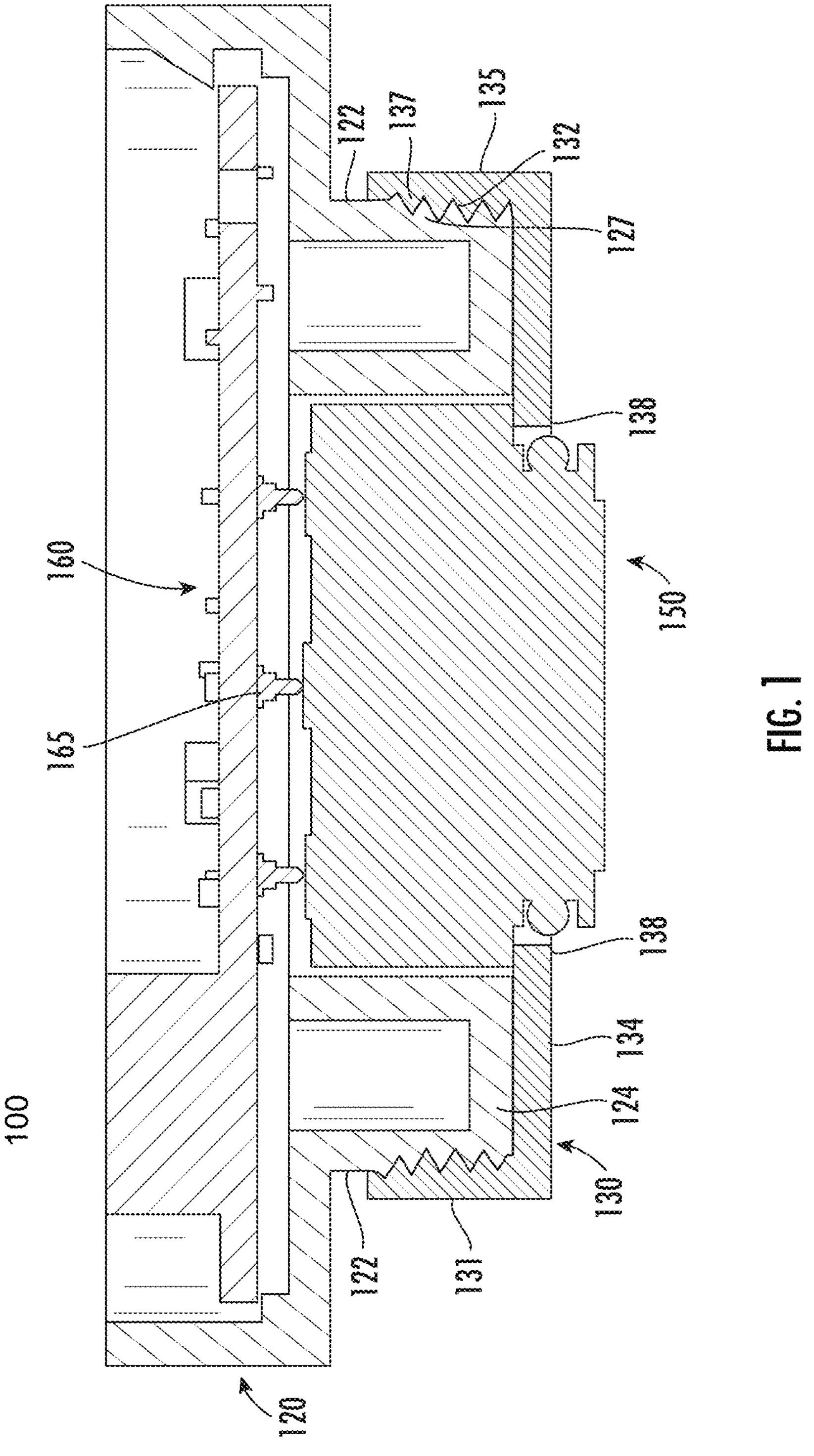
FIG. 1 is a schematic side view of an exemplary gas sensor assembly, in accordance with one or more embodiments.
Figure 2:
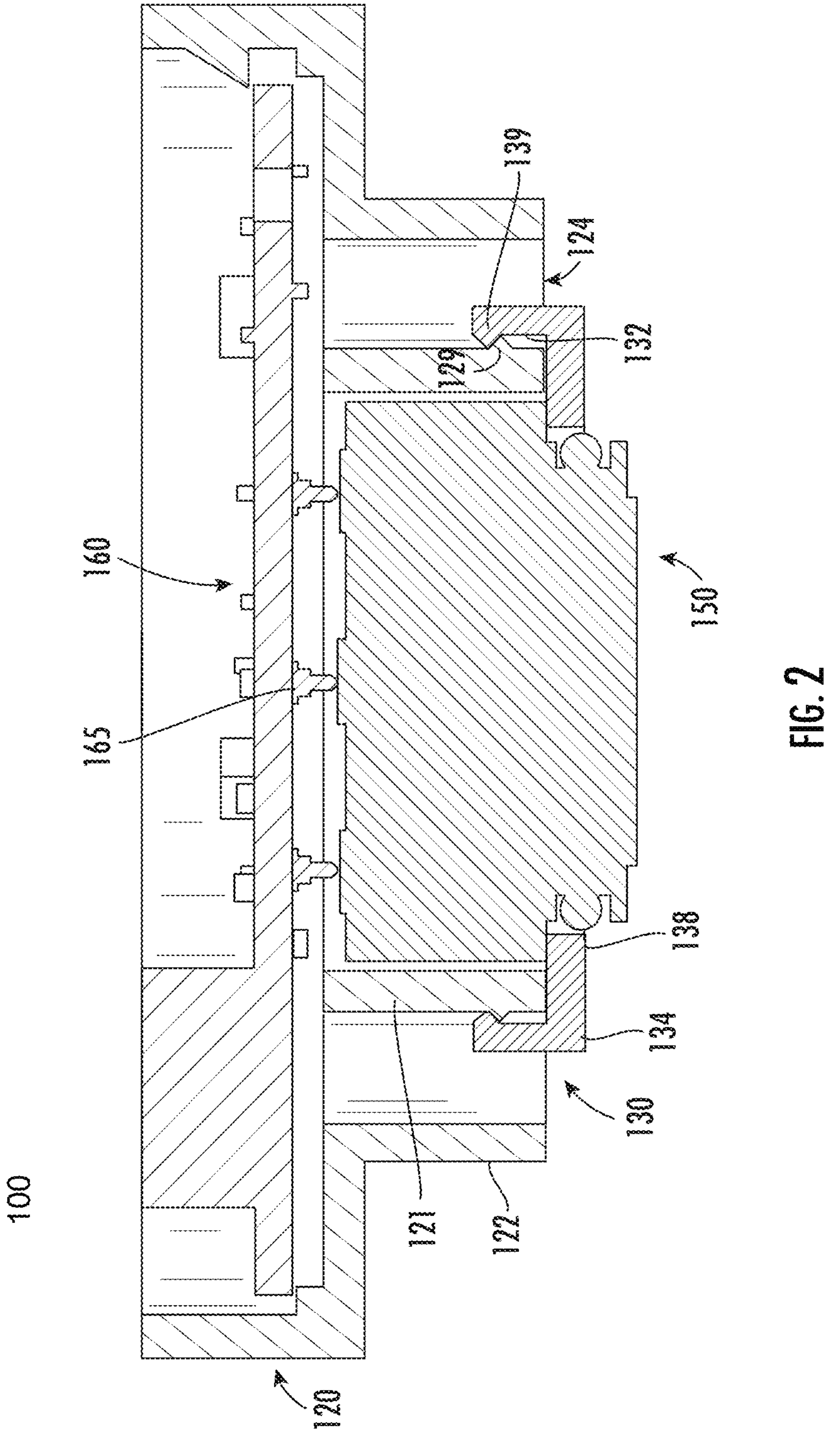
FIG. 2 is a schematic side view of an exemplary gas sensor assembly, in accordance with one or more embodiments.

FIG. 1 is a schematic side view of an exemplary gas sensor assembly 100, in accordance with one or more embodiments. In some embodiments, sensor assembly 100 may include a gas sensor 150, a sensor circuit 160, sensor housing 120, and a cover 130. Housing 120 may be configured to house one or more components of sensor assembly 100. For example, housing 120 may be configured to house at least a portion of gas sensor 150 and/or at least a portion of sensor circuit 160. Gas sensor 150 may be configured to be detachably connected to sensor circuit 160. In some embodiments, sensor circuit 160 may be a printed circuit board PCB configured for providing processing capabilities to gas sensor 150 and/or to the gas detector. In some embodiments, as shown in FIGS. 1-2, sensor circuit 160 may include one or more pins 165 (e.g., spring-loaded pins, pogo pins, pin and socket, etc.) configured to make electrical contact with a surface of sensor 150. Other types of electrical connection between gas sensor 150 and circuit 160 may be used and are compatible with the disclosure. As will be explained herein, cover 130 may help keep the electrical connection between sensor 150 and circuit 160.

In some embodiments, cover 130 may be configured to (or at least partially) cover an opening (of housing 120) that allows access to sensor 150 (to be removed and/or replaced). In some embodiments, housing 120 may be configured to detachably connect with cover 130. Cover 130 may be configured such that gas sensor 150 may be accessible (e.g., removable from sensor assembly 100) when cover 130 is disconnected (or at least partially disconnected) from housing 120. For example, if at least one component of cover 130 is disconnected from housing 120, gas sensor 150 may become accessible for removal. In another example, gas sensor 150 may become accessible if cover 130 is partially disconnected (e.g., not completely detached from housing 120). In some embodiments, sensor 150 may only be accessible if cover 130 is completely disconnected from housing 120.

In some embodiments, cover 130 may be configured to help hold sensor 150 in place inside housing 120. In some embodiments, cover 130 may be configured to maintain a connection between gas sensor 150 and sensor circuit 160. For example, cover 130 may be configured to apply a pressure (or a force) against gas sensor 150 to maintain connection between gas sensor 150 and sensor circuit 160. In these cases, in response to cover 130 being at least partially disconnected from sensor housing 120, gas sensor 150 is at least partially disconnected from sensor circuit 150. For example, in the case where cover 130 is threaded to housing 120 (as shown in FIG. 1) gas sensor 150 may lose connection with sensor circuit 160 when cover 130 starts unthreading from the housing. i.e., gas sensor 150 is disconnected from circuit 160 before cover 130 is completely disconnected (or removed).

Cover 130 and housing 120 may be connected at one or more connecting points or surfaces. For example, in some cases, connections may be made between one or more walls of the cover and housing 120, and/or connections may be made between a base of the cover and a bottom end of the housing. In the example shown in FIG. 1 housing 120 may include an outer wall 122 and a bottom end 124. In some embodiments, housing 120 and cover 130 may interface along a portion of outer wall 122, and/or a portion of bottom end 124. As explained below, housing 120 may be configured to connect with cover 130 in different ways. For example, in the example shown in FIG. 1, housing 120 may include one or more threads 127 on outer wall 122 (e.g., on a lower portion of outer wall 122 towards bottom end 124). Threads 127 may be configured to mate with corresponding threads on cover 130 to facilitate connection and disconnection.

In some embodiments, cover 130 includes a base element 134 and a projecting element 131. Projecting element 131 includes an inner wall 132 and outer wall 135. In some embodiments, inner wall 132 of projecting element 131 may include threads 137 (as shown in FIG. 1). Threads 137 are configured to mate with threads 127 of housing 120. FIG. 2 is a schematic side view of an exemplary gas sensor assembly 100, in accordance with one or more embodiments. FIG. 2 shows another example of connecting means between cover 130 and housing 120. In this example, a snap connection is made between cover 130 and an inner wall 121 of housing 120. In these embodiments, inner wall 132 of cover 130 may include a protruding element 139 configured to interface with a protruding element 129 on inner wall 121 of housing 120. Protruding elements 129 and 139 are configured to form a snap connection between the housing and the cover. In some embodiments, protruding element 129 may be located on outer wall 122, and the cover 130 may be configured such that inner wall 132 interfaces with outer wall 122 of the housing such that protruding elements 129 and 139 form a snap connection. In some examples, inner wall 121 (or outer wall 122) may include an indent or a hole (instead of the protruding element 129) configured for receiving protruding element 139 of inner wall 132. It is to be understood that the connecting examples described herein are for illustrative purposes only, other connecting means may be considered and are consistent with the present disclosure (e.g., bolts, screws, pins, fasteners, etc.).

Base element 134 may be configured to interface with (at least a portion of) bottom end 124 of housing 120. In some embodiments, the interface between base element 134 and housing 120 may include connecting means to connect base element 134 of cover 130 with housing 120. For example, in some embodiments, base element 134 may include one or more holes configured for receiving pins or screws to connect base element 134 to the housing 120 (e.g., via corresponding holes in bottom end 124). It will be understood by those skilled in the art that other connecting means may be used to connect base element 134 to housing 120. In some embodiments, base element 134 may be configured to extend (at least partially) inwardly beyond bottom end 124 to support sensor 150. For example, in some embodiments, base element 134 may be configured to extend beyond bottom 124 to form a shelf 138 for supporting at least a portion of sensor 150.

In some embodiments, base element 134 may include one or more shelves 138 that extend beyond bottom end 124. In other words, in these examples, base element 134 does not include a continuous shelf 138, but instead base element 134 includes one or more shelves 138 that extend from base element 134 beyond the bottom end 124 to support sensor 150 at multiple points. In some embodiments, one shelf 138 (partial shelf) may be enough to support sensor 150 and keep it in place. In other examples, more than one partial shelf 138 may be used, in these cases, the shelves may be spaced out around the base element. Removable cover 130 may attach to the sensor housing 120 in a way that does not require tools to remove and reattach. This may allow the user to replace only the sensor (without touching other components, such as the sensor circuit) rather than the entire assembly. This may be useful because the sensor is the only component in this assembly that requires replacing during the life of the product.

Cover 130 may have multiple configurations as described above. The examples shown in FIGS. 1-2 are for illustration purposes only, other configurations may be considered and are compatible with the present disclosure. For example, in some cases, cover 130 may be formed by a base element 134 only. In these cases, the base element 134 is configured for detachably connecting to housing 120 (e.g., via screws, bolts, pins, etc.). In these cases, cover 130 does not have a projecting element 131. Alternatively, in other examples, cover 130 may be in the form of one or more brackets configured to detachably connect with the housing (e.g., along the side wall of the housing, and/or the bottom end of the housing as described above). Each bracket may include a projecting of the bracket and a base element of the bracket, such that the base element of the bracket extends beyond the bottom end 124 of the housing to support sensor 150.

In some embodiments, one or more or more components of cover 130 may be made from metal, plastic, rubber, and/or other material that allow for the mechanical features of the cover as described herein. It is also to be noted that the above examples are for illustrative purposes only and is not intended to be limiting. It will be apparent to those skilled in the art in view of the present disclosure that other methods for removably connecting the cover and the sensor housing may be used and are consistent with the present disclosure.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every.

What is claimed is:

1. A gas sensor assembly comprising:

a gas sensor;

a sensor circuit;

a sensor housing, the sensor housing configured to house the gas sensor and the sensor circuit, wherein the gas sensor and the sensor circuit are configured to be detachably connected; and a cover, the cover configured to be detachably connected to the sensor housing, wherein the cover is configured to hold the gas sensor in place within the sensor housing;

wherein the cover is connected to a bottom of the sensor housing;

wherein the cover is configured to maintain a connection between the gas sensor and the sensor circuit, wherein responsive to the cover being partially disconnected from the sensor housing, the gas sensor is partially disconnected from the sensor circuit;

wherein the sensor circuit is configured to provide processing capabilities to the gas sensor.

2. The gas sensor assembly of claim 1, wherein the gas sensor is configured to be removed from the gas sensor assembly when the cover is disconnected from the sensor housing.

3. The gas sensor assembly of claim 1, wherein the cover is configured to apply a pressure against the gas sensor to maintain the connection between the gas sensor and the sensor circuit.

4. The gas sensor assembly of claim 1, wherein the cover comprises a base element, the base element configured to interface with a bottom end of the sensor housing, such that the base element extends inward to support a portion of the gas sensor.

5. The gas sensor assembly of claim 4, wherein the base element is configured to cover the bottom end of the sensor housing and extend inward beyond the bottom end to form a shelf to support the gas sensor.

6. The gas sensor assembly of claim 1, wherein the sensor housing comprises a side wall;

the cover comprises a projecting element; and the cover is configured to be detachably connected to the sensor housing such that the projecting element interfaces with a portion of the side wall.

7. The gas sensor assembly of claim 1, wherein the cover comprises a base element, the base element configured to interface with a bottom end of the sensor housing, wherein the base element comprises one or more shelves configured extend inward to support the gas sensor at one or more points.

8. The gas sensor assembly of claim 1, wherein the cover comprises one or more brackets configured to hold the gas sensor in place.

9. The gas sensor assembly of claim 1, wherein the sensor circuit comprises a printed circuit board including a plurality of pins configured to make electrical contact with the gas sensor.

10. The gas sensor assembly of claim 1, wherein the gas sensor extends through the cover.

11. A method of manufacturing a gas sensor assembly, the method comprising:

providing a sensor housing, the sensor housing configured to house a gas sensor and a sensor circuit, wherein the gas sensor and the sensor circuit are configured to be detachably connected; and providing a cover, the cover configured to be detachably connected to the sensor housing, wherein the cover is configured to hold the gas sensor in place within the sensor housing;

wherein the cover is connected to the bottom of the sensor housing;

wherein the cover is configured to maintain a connection between the gas sensor and the sensor circuit, wherein responsive to the cover being partially disconnected from the sensor housing, the gas sensor is partially disconnected from the sensor circuit;

wherein the sensor circuit is configured to provide processing capabilities to the gas sensor.

12. The method of claim 11, wherein the gas sensor is configured to be removed from the gas sensor assembly when the cover is disconnected from the sensor housing.

13. The method of claim 11, wherein the cover is configured to apply a pressure against the gas sensor to maintain the connection between the gas sensor and the sensor circuit.

14. The method of claim 11, wherein the cover comprises a base element, the base element configured to interface with a bottom end of the sensor housing, such that the base element extends inward to support a portion of the gas sensor.

15. The method of claim 14, wherein the base element is configured to cover the bottom end of the sensor housing and extend inward beyond the bottom end to form a shelf to support the gas sensor.

16. The method of claim 11, wherein the sensor housing comprises a side wall;

the cover comprises a projecting element; and the cover is configured to be detachably connected to the sensor housing such that the projecting element interfaces with a portion of the side wall.

17. The method of claim 11, wherein the cover comprises a base element, the base element configured to interface with a bottom end of the sensor housing, wherein the base element comprises one or more shelves configured to extend inward to support the gas sensor at one or more points.

18. The method of claim 11, wherein the cover comprises one or more brackets configured to hold the gas sensor in place.

* * * * *